US010518031B2

(12) United States Patent
Duke

(10) Patent No.: US 10,518,031 B2
(45) Date of Patent: Dec. 31, 2019

(54) BOLUS CALCULATOR WITH PROBABILISTIC GLUCOSE MEASUREMENTS

(71) Applicant: Roche Diabetes Care, Inc., Indianapolis, IN (US)

(72) Inventor: David L. Duke, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 395 days.

(21) Appl. No.: 15/061,526

(22) Filed: Mar. 4, 2016

(65) Prior Publication Data

US 2017/0252514 A1    Sep. 7, 2017

(51) Int. Cl.
    *G01N 33/50*    (2006.01)
    *A61M 5/172*    (2006.01)
    *G06F 19/00*    (2018.01)

(52) U.S. Cl.
    CPC ....... *A61M 5/1723* (2013.01); *G06F 19/3468* (2013.01); *G06F 19/3481* (2013.01); *A61M 2205/3584* (2013.01); *A61M 2205/52* (2013.01)

(58) Field of Classification Search
    None
    See application file for complete search history.

(56) References Cited

U.S. PATENT DOCUMENTS

| | | |
|---|---|---|
| 7,291,107 B2 | 11/2007 | Hellwig et al. |
| 8,579,854 B2 | 11/2013 | Budiman et al. |
| 8,579,879 B2 | 11/2013 | Palerm et al. |
| 8,734,422 B2 | 5/2014 | Hayter |
| 2004/0167464 A1 | 8/2004 | Ireland et al. |
| 2006/0047192 A1 | 3/2006 | Hellwig et al. |
| 2009/0105572 A1 | 4/2009 | Malecha |
| 2010/0262434 A1 | 10/2010 | Shaya |
| 2011/0071464 A1 | 3/2011 | Palerm |
| 2011/0184267 A1 | 7/2011 | Duke et al. |
| 2011/0257627 A1 | 10/2011 | Hovorka |
| 2011/0313674 A1 | 12/2011 | Duke et al. |
| 2012/0165638 A1 | 6/2012 | Duke et al. |
| 2012/0166126 A1 | 6/2012 | Engelhardt et al. |
| 2014/0005505 A1 | 1/2014 | Peyser et al. |
| 2014/0066884 A1 | 3/2014 | Keenan et al. |
| 2014/0066887 A1 | 3/2014 | Mastrototaro et al. |
| 2014/0083867 A1 | 3/2014 | Schaible |
| 2014/0088392 A1 | 3/2014 | Bernstein et al. |
| 2014/0100435 A1 | 4/2014 | Duke et al. |
| 2014/0118138 A1 | 5/2014 | Cobelli et al. |
| 2014/0187887 A1 | 7/2014 | Dunn et al. |
| 2014/0188400 A1 | 7/2014 | Dunn et al. |
| 2014/0235981 A1 | 8/2014 | Hayter |
| 2015/0273147 A1 | 10/2015 | Duke et al. |

FOREIGN PATENT DOCUMENTS

| | | |
|---|---|---|
| EP | 2762073 A1 | 8/2014 |
| WO | 2013/032965 A1 | 3/2013 |
| WO | 2014/106263 A2 | 7/2014 |
| WO | 2015/183689 A1 | 3/2015 |
| WO | 2015073211 A1 | 5/2015 |

OTHER PUBLICATIONS

International Search Report pertaining to Appln. No. PCT/US2017/019025, filed Feb. 23, 2017, 5 pages.
Written Opinion pertaining to Appln. No. PCT/US2017/019025, filed Feb. 23, 2017, 8 pages.
International Search Report pertaining to Appln. No. PCT/US2017/019013, filed Feb. 23, 2017, 5 pages.
Written Opinion pertaining to Appln. No. PCT/US2017/019013, filed Feb. 23, 2017, 8 pages.
U.S. Non-Final Office Action dated Sep. 5, 2017 pertaining to U.S. Appl. No. 14/677,148, 13 Pages.
International Search Report pertaining to PCT application No. PCT/US2017/031661, filed May 9, 2017, 6 pages.
Written Opinion pertaining to PCT application No. PCT/US2017/031661, filed May 9, 2017, 11 pages.
Kovatchev, B.P., et al., Symmetrization of the Blood Glucose Measurement Scale and Its Applications, Diabetes American Diabetes Association, vol. 20., No. 11, Nov. 1, 1997, pp. 1655-1658, USA.
International Search Report pertaining to PCT application No. PCT/US2017/031662, filed May 9, 2017, 6 pages.
Written Opinion pertaining to PCT application No. PCT/US2017/031662, filed May 9, 2017, 9 pages.
Hughes, et al., Hypoglycemia Prevention via Pump Attenuation and Red-Yellow-Green "Traffic" Lights Using Continuous Glucose Monitoring and Insulin Pump Data, Journal of Diabetes Science and Technology, vol. 4, No. 5, Sep. 1, 2010, pp. 1146-1155, USA.
Schwartz et al., "Use of Automated Bolus Calculators for Diabetes Management," Diabetes Management, Touch Medical Media 2013, 92-95.
International Search Report dated Aug. 21, 2017, pertaining to PCT/US2017/029072, filed Apr. 24, 2017, 6 pages.
Written Opinion dated Aug. 21, 2017, pertaining to PCT/US2017/029072, filed Apr. 24, 2017, 14 pages.
Jaramillo et al., Prediction of Postprandial Blood Glucose Under Intra-Patient Variability and Uncertainty and Its Use in the Design of Insulin Disposing Strategies for Type I Diabetic Patients, Jul. 22, 2011, pp. 1-178, URL:http://dugi-doc.udg.edu/bitstream/handle.
International Search Report pertaining to Appln. No. PCT/US2017/019030, filed Feb. 23, 2017, 5 pages.

(Continued)

*Primary Examiner* — Jason M Sims
(74) *Attorney, Agent, or Firm* — Dinsmore & Shohl, LLP

(57) ABSTRACT

Methods and devices involving using a bolus calculator for calculating a correction insulin dose accounting for continuous glucose monitoring noise. More specifically, methods and devices using an algorithm executed by a processor of the bolus calculator and using a glucose measurement and uncertainty of the glucose measurement to determine if a standard correction dose should be adjusted once calculations are performed for the standard correction dose and hypoglycemia-averse correction insulin dose and the two doses are compared.

23 Claims, 5 Drawing Sheets

(56) References Cited

OTHER PUBLICATIONS

Written Opinion pertaining to Appln. No. PCT/US2017/019030, filed Feb. 23, 2017, 9 pages.
U.S. Non-Final Office Action dated May 31, 2018 pertaining to U.S. Appl. No. 15/170,468, 12 pages.

BOLUS CALCULATOR WITH PROBABILISTIC GLUCOSE MEASUREMENTS

TECHNICAL FIELD

This application relates generally to methods and devices involving using a bolus calculator for calculating a correction insulin dose accounting for continuous glucose monitoring (CGM) noise. More specifically it relates to methods and devices using an algorithm executed by a processor of the bolus calculator and using a glucose measurement and uncertainty of the glucose measurement to determine if a standard correction dose should be adjusted once calculations are performed for the standard correction dose and a hypoglycemia-averse correction insulin dose and the two doses are compared.

BACKGROUND

Diabetes can be characterized by hyperglycemia and relative insulin deficiency. There are two main types of diabetes, Type I diabetes (insulin-dependent diabetes mellitus) and Type II diabetes (non-insulin-dependent diabetes mellitus). In some instances, diabetes is also characterized by insulin resistance.

Insulin secretion functions to control the level of blood glucose to keep the glucose levels at an optimum level. Healthcare may involve both establishing a therapeutic program and monitoring the progress of the afflicted person. Monitoring blood glucose levels is an important process that is used to help diabetics maintain blood glucose levels as near to normal as possible throughout the day. Monitoring can also allow successful treatment of a diabetic by altering therapy as necessary. Monitoring may allow the diabetic to more closely follow his or her condition and, in addition, can provide information of value to the healthcare provider in determining both progress of the patient and detecting any need to change the patient's therapy program.

There are two main types of blood glucose monitoring systems used by patients: single point (or non-continuous) systems and continuous systems. Non-continuous systems consist of meters and tests strips and require blood samples to be drawn from fingertips or alternate sites, such as forearms and legs. An example of a noncontinuous system may require a diabetic to apply a blood sample to a reagent-impregnated region of a test strip, wipe the blood sample from the test strip after a predetermined period of time, and determine a blood glucose level by comparing the color of the reagent-impregnated regions of the test strip with a color chart supplied by the test strip manufacturer. Alternatively, many patients use CGM to monitor their glucose level on an ongoing basis. In order to perform CGM, a glucose sensor may be placed under the skin which is capable of measuring the glucose level of the person in the interstitial fluid. The glucose sensor may periodically measure the glucose level of the person at a known time interval, such as every minute, and transmit the results of the glucose measurement result to an electronic monitor.

Individuals with diabetes are currently using CGM to calculate correction boluses using the same equations designed for self-monitoring of blood glucose levels. This increases the risk of hypoglycemia due to the increased uncertainty of CGM. Embodiments described herein provide for safer methods for calculating correction boluses. Embodiments detail calculations using an algorithm that improving the accuracy of the bolus calculator by accounting for continuous glucose monitoring (CGM) noise.

SUMMARY

Embodiments described herein provide for a method for calculating a correction insulin dose accounting for continuous glucose monitoring noise comprising: providing a bolus calculator containing therewithin a processor that when activated executes an algorithm; activating the processor to execute the algorithm; calculating, via the algorithm, a standard correction insulin dose ($I_g$) utilizing an insulin sensitivity factor (IS) of a user and a pre-set target glucose level; calculating, via the algorithm, a hypoglycemia-averse correction insulin dose ($I_{hypo(x)\%}$) using the insulin sensitivity factor of the user, a provided glucose measurement of the user, and a measure of an uncertainty of the glucose measurement; and selecting the minimum value between the hypoglycemia-averse correction insulin dose and the standard correction insulin dose to adjust an insulin bolus for a meal.

Additional embodiments described herein provide for a method of using a bolus calculator for calculating a correction insulin dose accounting for continuous glucose monitoring noise, the method comprising: providing the bolus calculator containing therewithin a processor that when activated executes an algorithm defining a pre-set target glucose level ($g_t$), a threshold percentage defining a probability of hypoglycemia ($P_{hypo}$), and a standard deviation ($\sigma_g$) defining an uncertainty of a glucose measurement (g); activating the processor to execute the algorithm; calculating, using the glucose measurement, the standard deviation, and a parameter on a normal cumulative distribution, a level ($g_{x\%}$), wherein x corresponds to the threshold percentage defining the probability of hypoglycemia; determining if the standard correction dose should be adjusted by: calculating a standard correction insulin dose ($I_g$) utilizing an insulin sensitivity factor (IS) of a user and the pre-set target glucose level; calculating a hypoglycemia-averse correction insulin dose ($I_{hypo(x)\%}$) using the insulin sensitivity factor of the user and the calculated level on the normal cumulative distribution; comparing the standard correction insulin dose with the hypoglycemia-averse correction insulin dose; and selecting the minimum of the correction insulin doses; and adjusting a corresponding meal insulin bolus via the selected insulin dose so as to provide the continuous glucose monitoring noise accounting.

Yet additional embodiments described herein provide for a bolus calculator to calculate a correction insulin dose to account for continuous glucose monitoring noise comprising: a processor that when activated is configured to: execute an algorithm defining a pre-set target glucose level ($g_t$), a threshold percentage defining a probability of hypoglycemia ($P_{hypo}$), and a standard deviation ($\sigma_g$) defining an uncertainty of a glucose measurement (g); calculate, using the glucose measurement and the standard deviation, a level ($g_{x\%}$) on a normal cumulative distribution, wherein x corresponds to the threshold percentage defining the probability of hypoglycemia; determine if the standard correction dose should be adjusted by: calculating a standard correction insulin dose ($I_g$) utilizing an insulin sensitivity factor (IS) of a user and the pre-set target glucose level; calculating a hypoglycemia-averse correction insulin dose ($I_{hypo(x)\%}$) using the insulin sensitivity factor of the user and the calculated level on the blood glucose cumulative frequency distribution; comparing the standard correction insulin dose with the hypoglycemia-averse correction insulin dose; and select the minimum of the correction insulin doses; and adjust a corresponding meal insulin bolus via the selected insulin dose so as to provide the continuous glucose monitoring noise accounting.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION

Specific embodiments of the present disclosure will now be described. The invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which embodiments of this invention belong. The terminology used herein is for describing particular embodiments only and is not intended to be limiting of the invention. As used in the specification and appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about," which is intended to mean up to plus or minus 10% of an indicated value. Additionally, the disclosure of any ranges in the specification and claims are to be understood as including the range itself and also anything subsumed therein, as well as endpoints. Unless otherwise indicated, the numerical properties set forth in the specification and claims are approximations that may vary depending on the desired properties sought to be obtained in embodiments of the present invention. Notwithstanding that numerical ranges and parameters setting forth the broad scope of embodiments of the invention are approximations, the numerical values set forth in the specific examples are reported as precisely as possible. Any numerical values, however, inherently contain certain errors necessarily resulting from error found in their respective measurements.

Parts of methods described herein such as mathematical determinations, calculations, inputting of data for computations or determinations of equations or parts thereof can be performed on parts of or one or more computers or computer systems that can include one or more processors, as well as software to run or execute programs and run calculations or computations.

Methods and systems and parts thereof described herein can be combined so as to implement embodiments of the invention. Forms of words used herein can have variations: for example when a word such as "calculate" is used, this implies that variations such as "calculated" and "calculating" are understood and have been considered.

As user herein, "user," "patient," and "person" are used to refer to an individual interacting with the CGM system to improve that individual's health via improvements described herein.

Figure 1:
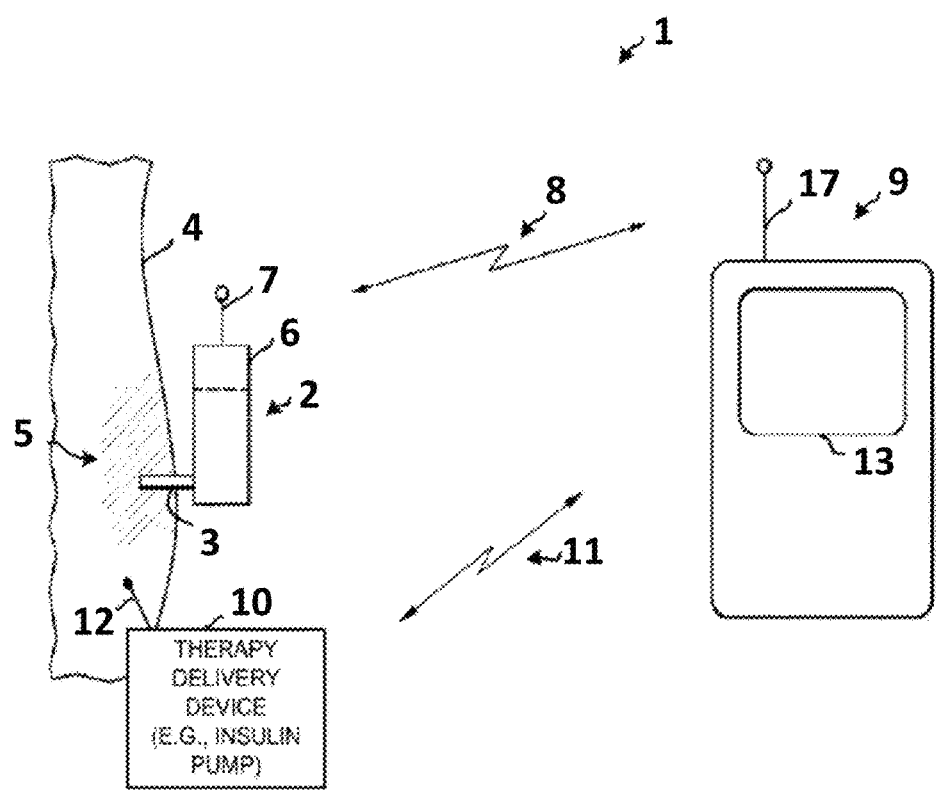
FIG. 1 illustrates the CGM system according to one or more embodiments described herein.

Referring to FIG. 1, an exemplary CGM system 1 is illustrated for monitoring the glucose level of a person having diabetes. In particular, the CGM system 1 is operative to collect a measured glucose value at a predetermined, adjustable interval, such as every one minute, five minutes, or at other suitable intervals. The CGM system 1 illustratively includes a glucose sensor 2 having a needle or probe 3 that is inserted under a skin 4 of the person. The end of the needle 3 is positioned in a region containing an interstitial fluid 5 such that measurements taken by the glucose sensor 2 are based on the level of glucose in the interstitial fluid 5. The needle can also be placed in a region with blood and/or other bodily fluid. The glucose sensor 2 is positioned adjacent the abdomen of the person or at another suitable location. The glucose sensor 2 may comprise other components as well, including but not limited to a wireless transmitter 6 and an antenna 7. The glucose sensor 2 may alternatively use other suitable devices for taking measurements, such as, for example, a non-invasive device (e.g., an infrared light sensor). Upon taking a measurement, the glucose sensor 2 transmits the measured glucose value(s) via a communication link 8 to a computing device 9, illustratively a blood glucose management device 9 or a bolus calculator 9 (in specific embodiments the bolus calculator has a housing, as described herein, and is a stand-alone device, working in conjunction with the processor(s) 14 which includes the bolus calculator module 19 performing logic properties of, for example, the bolus calculator 9).

The CGM system 1 further includes a therapy delivery device 10, illustratively an insulin infusion pump 10, for delivering therapy (e.g., insulin) to the person. The pump 10 can have a single housing or can have a two-part housing where one part is reusable and the other disposable, where the disposable part can include a power source such as a battery. The insulin pump 10 is in communication with the management device 9 via a communication link 11, and the management device 9 is able to communicate bolus and basal rate information to the insulin pump 10. The insulin pump 10 includes a catheter 12 having a needle that is inserted through the skin 4 of the person for injecting the insulin. Insulin pump 10 is illustratively positioned adjacent the abdomen of the person or at another suitable location. Similar to the glucose sensor 2, the infusion pump 10 also includes a wireless transmitter and an antenna for communication with management device 9. The insulin pump 10 is operative to deliver basal insulin (e.g., small doses of insulin continuously or repeatedly released at a basal rate) and bolus insulin (e.g., a surge dose of insulin, such as around a meal event, for example). The bolus insulin may be delivered in response to a user input triggered by the user, or in response to a command from management device 9. Similarly, the basal rate of the basal insulin is set based on user input or in response to a command from management device 9. Infusion pump 10 may include a display 13 for displaying pump data and a user interface providing user controls. In an alternative embodiment, insulin pump 10 and the glucose sensor 2 may be provided as a single device worn by the patient, and at least a portion of the logic provided by a processor 14 (FIG. 2) may reside on this single device. Bolus insulin may also be injected by other means, such as manually by the user via a needle.

Communication links 8, 11 are illustratively wireless, such as a radio frequency ("RF") or other suitable wireless frequency, in which data and controls are transmitted via electromagnetic waves between the sensor 2, the therapy delivery device 10, and the management device 9. Bluetooth® is one exemplary type of wireless RF communication system that uses a frequency of approximately 2.4 Gigahertz (GHz). Another exemplary type of wireless communication scheme uses infrared light, such as the systems supported by the Infrared Data Association® (IrDA®). Other suitable types of wireless communication may be provided. Furthermore, each communication link 8, 11 may facilitate communication between multiple devices, such as between the glucose sensor 2, the computing device 9, the insulin pump 10, and other suitable devices or systems. Wired links may alternatively be provided between devices of the system 1, such as, for example, a wired Ethernet link. Other suitable public or proprietary wired or wireless links may be used.

Figure 2:
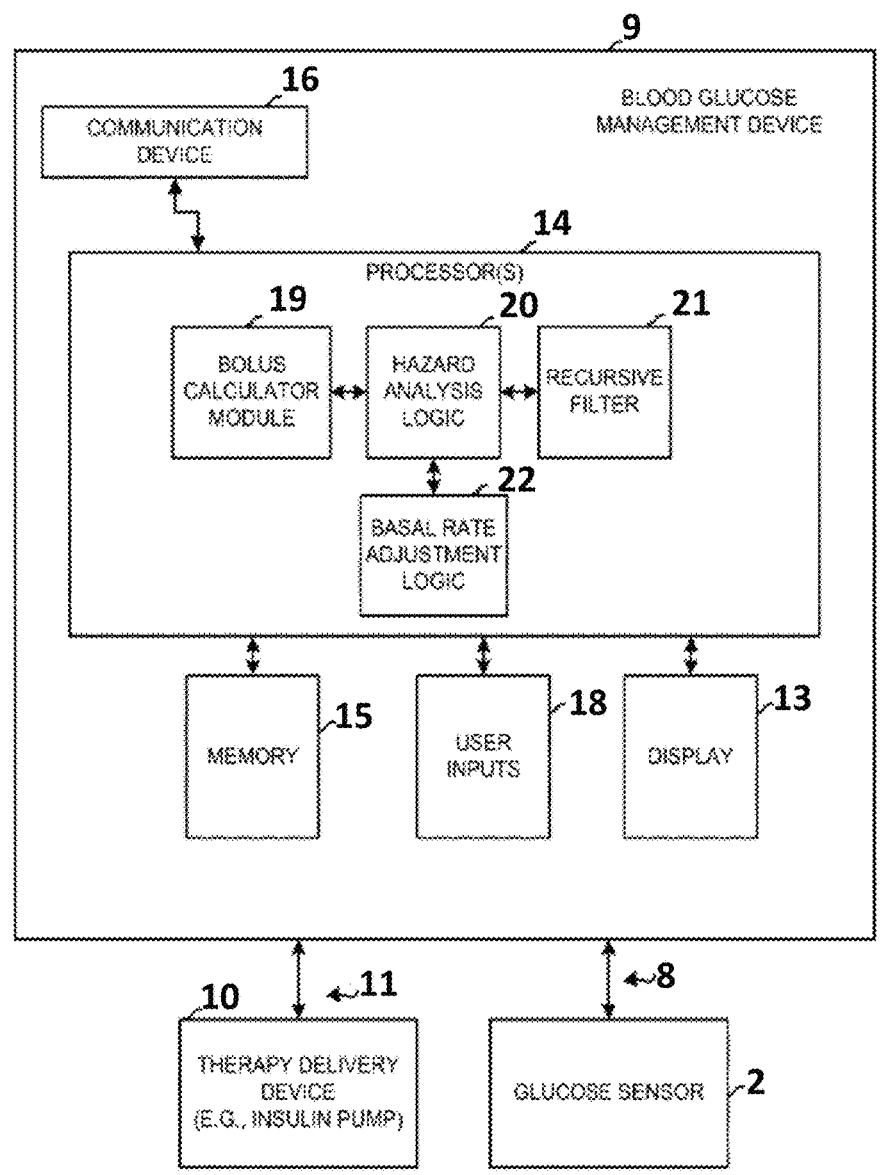
FIG. 2 illustrates an exemplary blood glucose management device, therapy delivery device, and glucose sensor of the CGM system of FIG. 1, the blood glucose management device including a bolus calculator module, hazard analysis logic, a basal rate adjustment logic, and a recursive filter.

FIG. 2 illustrates an exemplary embodiment of the management device 9 of the CGM system 1 of FIG. 1. The management device 9 includes at least one processing device 14 that executes software and/or firmware code stored in a memory 15 of management device 9. The software/firmware code contains instructions that, when executed by the processor 14 of the management device 9, causes the management device 9 to perform the functions described herein. The management device 9 may alternatively include one or more application-specific integrated circuits (ASICs), field-programmable gate arrays (FPGAs), digital signal processors (DSPs), hardwired logic, or combinations thereof. While the management device 9 is illustratively a glucose monitor 9, other suitable management devices 9 may be provided, such as, for example, desktop computers, laptop computers, computer servers, personal data assistants ("PDA"), smart phones, cellular devices, tablet computers, infusion pumps, an integrated device including a glucose measurement engine and a PDA or cell phone, etc. Although the management device 9 is illustrated as a single management device 9, multiple computing devices may be used together to perform the functions of the management device 9 described herein. FIG. 2 can also include the bolus calculator module 19, a hazard analysis logic component 20 (such as for accounting for time/rates of change of glucose levels in calculations), a recursive filter 21 (such as for removing noise in calculations or adjusting for the probability of glucose sensor accuracy), and/or a basal rate adjustment logic component 22 (such as for adjusting for the effect of the user activities on rates in calculations).

The memory 15 is any suitable computer readable medium that is accessible by the processor 14. The memory 15 may be a single storage device or multiple storage devices, may be located internally or externally to the management device 9, and may include both volatile and non-volatile media. Further, the memory 15 may include one or both of removable and non-removable media. Exemplary memory 15 includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by the management device 9.

The management device 9 further includes a communication device 16 operatively coupled to processor 14. The communication device 16 includes any suitable wireless and/or wired communication module operative to transmit and receive data and controls over the communication links 8, 11 between the device 9 and the glucose sensor 2 and the insulin pump 10. In one embodiment, the communication device 16 includes an antenna 17 (FIG. 1) for receiving and/or transmitting data wirelessly over the communication links 8, 11. The management device 9 stores in the memory 15 measured glucose results and other data received from the glucose sensor 2 and/or the insulin pump 10 via the communication device 16.

The management device 9 includes one or more user input devices 18 for receiving user input. The input devices 18 may include pushbuttons, switches, a mouse pointer, keyboard, touch screen, or any other suitable input device. The display 13 is operatively coupled to the processor 14. The display 13 may comprise any suitable display or monitor technology (e.g., liquid crystal display, etc.) configured to display information provided by the processor 14 to the user. Processor 14 is configured to transmit to the display 13 information related to the detected glucose state of the person, the risk associated with the glucose state, and basal rate and bolus information. The glucose state may include the estimated glucose level and/or the estimated rate-of-change of the glucose level, as well as an estimate of the quality or uncertainty of the estimated glucose level. Moreover, the displayed information may include warnings and/or alarms, etc. regarding whether the estimated or predicted glucose level of the person is hypoglycemic or hyperglycemic. For example, a warning may be issued if the person's glucose level falls below (or is predicted to fall below) a predetermined hypoglycemic threshold, such as from about 50 to about 70 mg/dL of glucose in blood. Management device 9 may also be configured to communicate information or warnings to the person via a sense of touch, such as for example by vibrating.

In one embodiment, management device 9 is in communication with a remote computing device, such as at a caregiver's facility or a location accessible by a caregiver, and data (e.g., glucose data or other physiological information) is transferred between them. In this embodiment, management device 9 and the remote device are configured to transfer physiological information through a data connection such as, for example, via the Internet, cellular communications, or the physical transfer of a memory device such as a diskette, USB key, compact disc, or other portable memory device.

Specific embodiments of methods and devices as described herein can include calculations for a level ($g_{x\ \%}$) involving calculating, using the glucose measurement, the standard deviation, and a parameter on a normal cumulative distribution, a level ($g_{x\ \%}$), wherein x corresponds to the threshold percentage defining the probability of hypoglycemia. Specific embodiments can include defining the ($g_{x\%}$) as ($g_{5\%}$) and performing the following calculation: $g_{5\%} = g - 1.6449 \cdot \sigma_g$. In other specific embodiments ($g_{x\%}$) can be defined such that the x represents up to about twenty-five percent or up to about thirty percent. In yet other embodiments the x value can be about five percent, about ten percent, about fifteen percent, about twenty percent, about twenty-five percent, or about thirty percent. In yet other embodiments the x value can be selected from a range from about five percent to about ten percent or from about one percent to about ten percent, or from about one percent to about twenty percent.

In specific embodiments the parameter −1.6449 on the blood glucose cumulative frequency distribution equal to five percent. Other parameters that can be used for ($g_{x\%}$) calculations, with associated percentages (that can be used for x) are: −1.28155 for ten percent, −1.751 for four percent, −1.96 for two-point five percent, −2.326 for one percent, and/or −2.576 for one-half percent. The bolus calculator module 19 can automatically select, via the processor 14, between the percentages, also using the percentages to set a pre-set threshold percentage defining a probability of hypoglycemia ($P_{hypo}$).

Specific embodiments of methods and devices as described herein can include various calculations and settings. For example, methods and devices can include setting the ($g_t$) as $$g_t = 110 \frac{\text{mg}}{\text{dl}}.$$

Embodiments can comprise setting a hypoglycemia threshold at $$T_{hypo} = 70 \frac{\text{mg}}{\text{dl}}$$

and subtracting the ($T_{hypo}$) from the ($g_{x\%}$) in the calculation of the hypo-glycemia-averse correction insulin dose ($I_{hypo(x)\%}$). Embodiments can comprise calculating the standard correction insulin dose by:

$$I_g = \frac{(g - g_t)}{IS}.$$

Additional embodiments can comprise defining the ($g_{x\%}$) as ($g_{5\%}$), designating the ($I_{hypo(x)\%}$) as ($I_{hypo5\%}$) and calculating the hypoglycemia-averse correction insulin dose by:

$$I_{hypo5\%} = \frac{g_{5\%} - T_{hypo}}{IS},$$

wherein IS is the insulin sensitivity factor for the user.

Following a bolus event, the bolus calculations must account for active insulin recently injected into the body. One method for handling active insulin is to shift the glucose target (g) by the glucose equivalent for the active insulin ($g_i$): $\hat{g}_t = g_t + g_i$. The hypoglycemia threshold must also be shifted ($T_{hypo}$) by the glucose equivalent for the active insulin ($g_i$): $\hat{T}_{hypo} = T_{hypo} + g_i$. The glucose equivalent of the active insulin may also include a glucose range for the expected rise in glucose following a meal. The standard correction insulin dose is then calculated by:

$$I_g = \frac{g - \hat{g}_t}{IS}$$

and the hypoglycemia-averse correction insulin dose by:

$$I_{hypo5\%} = \frac{g_{5\%} - \hat{T}_{hypo}}{IS}.$$

For a further description of additional features that may be provided by the bolus calculator module 19, see U.S. patent application Ser. No. 13/593,557, filed on Aug. 24, 2012, entitled "Handheld Diabetes Management Device with Bolus Calculator," and U.S. patent application Ser. No. 13/593,575, filed on Aug. 24, 2012, entitled "Insulin Pump and Methods for Operating the Insulin Pump," the entire disclosures of which are incorporated by reference herein.

In specific embodiments methods comprise removing the corresponding meal bolus when the selected insulin dose is negative. Methods can also include a carbohydrate suggestion when the selected insulin dose is negative.

In specific embodiments methods comprise coupling the bolus calculator with a database such that the algorithm accounts for past uncertainty regarding at least one of a calibration routine of the user, a day of use for a sensor, and a sensor lot.

Methods and devices described herein can be used instead of or with a system in conjunction with methods described in U.S. patent application Ser. No. 14/677,148 which is hereby incorporated by reference in its entirety.

Specific embodiments herein comprise an alert. More specifically, the alert is customizable and can be a visual alert, such as a displayed icon or message, or light, an audible alert, such as a beep or music, or a vibrational alert, or a combination thereof. The alert can have single and/or multiple modes of notification. For example, the alert can simultaneously include an audible, visual, and vibrational notification. When an event triggers the alert notification, the user may be notified of the event or condition by feeling the vibration, hearing the audible alert, and/or seeing the visual alert.

In one example, an event or a pattern can trigger an alert that can be used to alert the patient to take specific actions whenever a particular event occurs. For example, the pattern can be a post-prandial event, hypoglycemic event, exercise, meals, etc. or any other problematic event or pattern that has occurred in the patient's past physiological data. Thus, when the event is detected again on a real-time basis, the system 1 will alert the patient to that fact such as via the display 13 and/or vibration and/or noise. The bolus calculator can have the processor 14 or multiple processors 14 (including the bolus calculator module 19) interacting with various hardware and/or software to send the alert to a clinician if the person's glucose level falls below (or is predicted to fall below) a predetermined hypoglycemic threshold; an alert can also be sent if the measure of uncertainty is above a certain point. The bolus calculator can be configured to transmit the alert wirelessly and activate an application on the clinician's computer when the computer comes online and/or is otherwise turned on/activated.

EXAMPLES

Utilization of the Algorithm

A glucose measurement estimate is provided along with a measure of its uncertainty. The method uses the bolus calculator in the form of an algorithm that is processed by the processor 14 or multiple processors 14 (including the bolus calculator module 19). In specific examples this includes the standard deviation, though a variance can be used. The method uses the bolus calculator. In specific embodiments the threshold percentage defining the probability of hypoglycemia ($P_{hypo}$) value is provided as below:

$$P_{hypo}=5\%$$

$$P_{hypo}=5\%$$

The target glucose level ($g_t$) and the hypoglycemia threshold ($T_{hypo}$) are defined as indicated below:

$$g_t = 110 \frac{mg}{dl}$$

$$T_{hypo} = 70 \frac{mg}{dl}$$

In this example the algorithm is providing a glucose measurement estimate and a standard deviation (g, $\sigma_g$) that defines the uncertainty. Also provided for utilization by the algorithm is the user's insulin sensitivity, IS.

Methods described herein can include a step to identify if the standard correction bolus should be adjusted to reduce the hypoglycemia risk. This occurs if the actual glucose measurement is overestimated. A calculation can be provided as below:

$$g_{5\%}=g-1.6449\cdot\sigma_g.$$

The parameter −1.6449 on the normal cumulative distribution is equal to five percent. In specific embodiments methods use a relative error bounds.

Then the standard correction insulin dose and the hypoglycemia-averse correction dose are calculated. The standard dose divides the difference between the current glucose value and target by the insulin sensitivity factor, as illustrated below.

$$I_g = \frac{(g-g_t)}{IS}.$$

The hypoglycemia-averse method assumes an overestimated glucose measurement and accounts for the hypo threshold.

$$I_{hypo5\%} = \frac{g_{5\%} - T_{hypo}}{IS}$$

If the value for $I_{hypo5\%}$ is less than $I_g$ then $I_{hypo5\%}$ is used as the correction, as illustrated below:

$$I=\min(I_g, I_{hypo5\%}).$$

If the recommended insulin is negative then it could be removed from a corresponding meal bolus or, if there is no associated meal bolus, then a carbohydrate suggestion can be given.

Results

Figure 3:
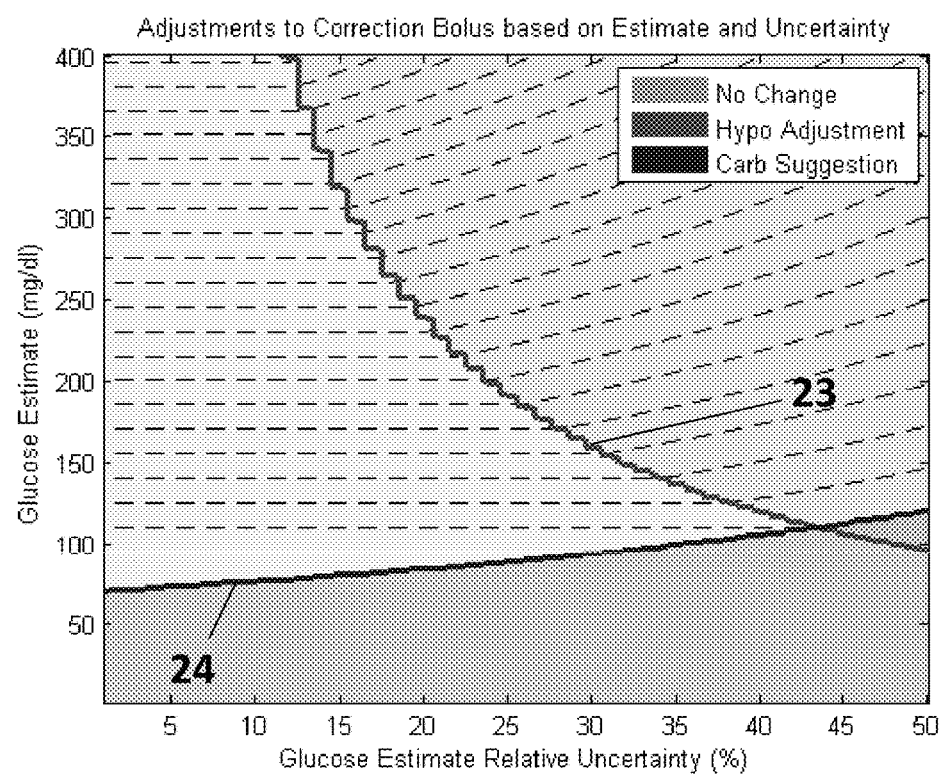
FIG. 3 illustrates a graph of the glucose estimate versus the glucose estimate relative uncertainty, and outlines example correction bolus advice via lines and regions for an individual with an insulin sensitivity factor of 30 milligrams per deciliter per international unit (mg/dl/IU)
Figure 4:
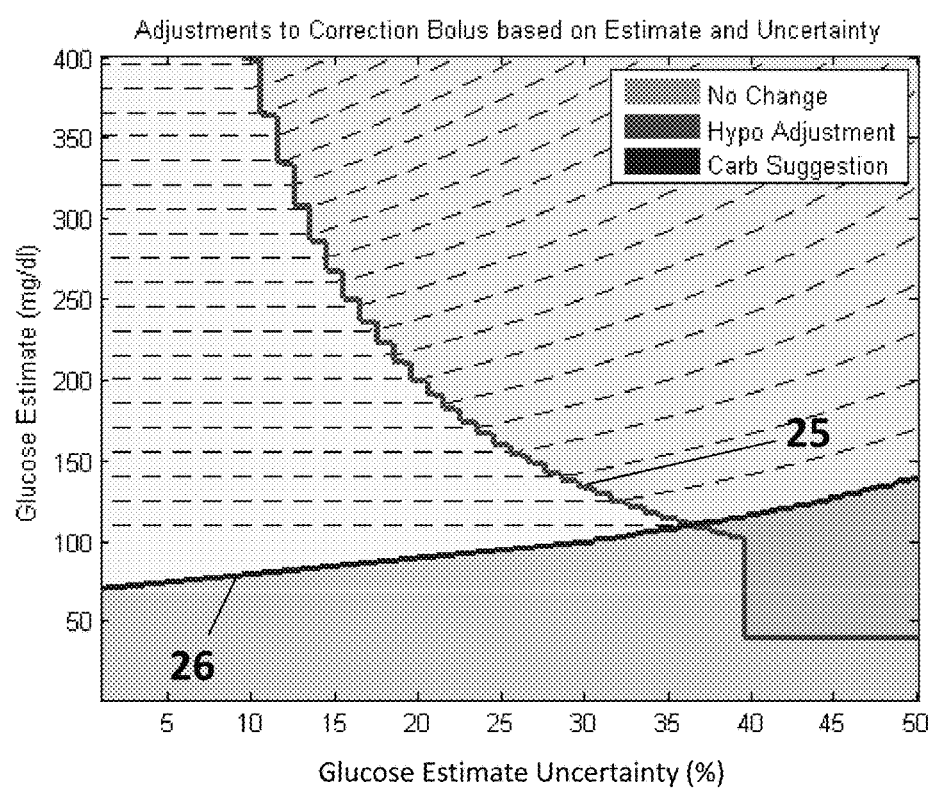
FIG. 4 illustrates a graph of the glucose estimate versus the glucose estimate uncertainty, and outlines example correction bolus advice via lines and regions for an individual as in FIG. 3 when the uncertainty of the glucose measurement is expressed as a relative value above 100 mg/dL and as an absolute value below 100 mg/dL.

FIG. 3 shows the correction bolus advice for an individual with an insulin sensitivity factor of 30 mg/dL/IU. When the uncertainty is lower there is no change to the bolus advice. When the relative uncertainty increases the probability of hypoglycemia rises above five percent and a reduction of the correction bolus occurs. Also, as the uncertainty increases, the glucose value that triggers a carbohydrate suggestion increases (line 24); the graph also shows a hypoglycemia adjustment line at 23. FIG. 4 illustrates a graph of the glucose estimate versus the glucose estimate relative uncertainty, and outlines example correction bolus advice via lines and regions for an individual as in FIG. 3 when the uncertainty of the glucose measurement is expressed as a relative value above 100 mg/dL and as an absolute value below 100 mg/dL. More specifically, as the uncertainty increases, the glucose value that triggers a carbohydrate suggestion increases (line 26); the graph also shows a hypoglycemia adjustment line at 25. This method could be paired with algorithms that account for the rate-of-change when calculating the correction bolus. Results of the algorithm as described herein can be provided on the display (displayed on the display).

Figure 5:
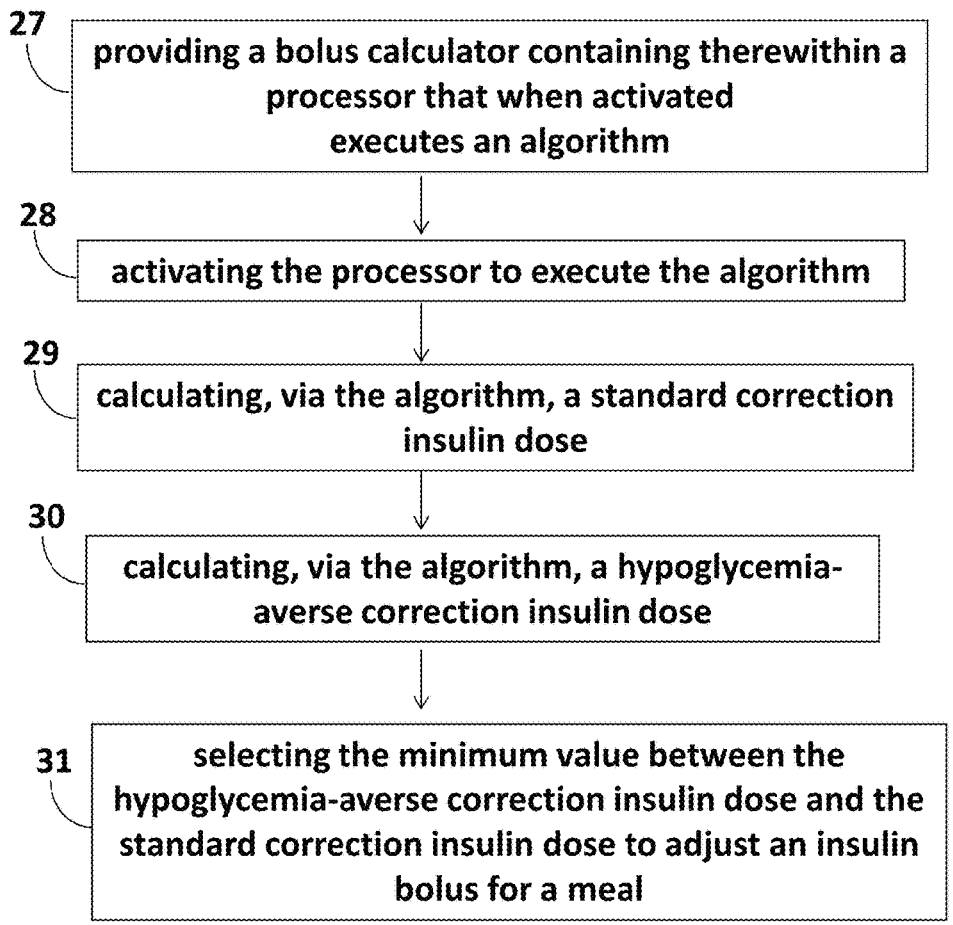
FIG. 5 illustrates a flowchart outlining a method of embodiments provided herein.

The uncertainty of a glucose measurement can be expressed as a relative value above 100 mg/dL and below an absolute value. For example, a 10-10 system is within plus or minus 10 mg/dL below 100 mg/dL and within plus or minus 10% above. If this method for expressing uncertainty is used then the results change to those illustrated in FIG. 4. The threshold for carbohydrate suggestion is raised due to the absolute uncertainty being larger than the relative value in the region below 100 mg/dL. FIG. 5 illustrates a flowchart outlining a method of embodiments provided herein (27-31).

Uncertainty as described herein could come from one or more of: the filter, calibration routine, day of use for the sensor, sensor lot, and previous sensors worn by the individual, etc., or combinations thereof.

Embodiments detail calculations using an algorithm that improve the accuracy of the bolus calculator by accounting for continuous glucose monitoring (CGM) noise. As it is believed that other known methods do not account for such noise there is less accuracy in such devices prior to the current embodiments of the invention; additionally, the calculations can be more quickly performed and displayed as the calculations specifically account for CGM use.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, versions, geometries, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

What is claimed is:

1. A method of adjusting a standard correction insulin bolus administered to a user to reduce hypoglycemia risk after consuming a corresponding meal via accounting for continuous glucose monitoring noise of a sensor imbedded in the user, the method comprising:
   coupling a bolus calculator to a database, the bolus calculator containing therewithin a processor that when activated executes an algorithm;
   activating the processor to execute the algorithm;
   calculating, via the algorithm, a standard correction insulin dose ($I_g$) utilizing an insulin sensitivity factor (IS) of a user and a pre-set target glucose level;
   receiving by the bolus calculator a glucose measurement from the sensor imbedded in the user;
   calculating, via the algorithm, a hypoglycemia-averse correction insulin dose ($I_{hypo(x)\%}$) using the insulin sensitivity factor, the received glucose measurement of the user, and a measure of an uncertainty of the glucose measurement from the sensor, wherein the algorithm accounts for past uncertainty regarding at least one of a calibration routine of the user, a day of use for the sensor, and a sensor lot via the database; and
   adjusting the standard correction insulin bolus administered to the user for the corresponding meal via selecting the minimum value between the hypoglycemia-averse correction insulin dose and the standard correction insulin dose to reduce hypoglycemia risk of the user after consuming the corresponding meal.

2. A method of adjusting a standard correction insulin bolus administered to a user to reduce hypoglycemia risk after consuming a corresponding meal via accounting for continuous glucose monitoring noise of a sensor imbedded in the user, the method comprising:
   coupling a bolus calculator to a database, the bolus calculator containing therewithin a processor that when activated executes an algorithm defining a pre-set target glucose level ($g_t$), a threshold percentage defining a probability of hypoglycemia ($P_{hypo}$), and a standard deviation ($\sigma_g$) defining an uncertainty of a glucose measurement (g) received from the sensor imbedded in the user;
   activating the processor to execute the algorithm;
   receiving by the bolus calculator the glucose measurement from the sensor of the user;
   calculating, using the glucose measurement, the standard deviation, and a parameter on a normal cumulative distribution, a level ($g_{x\%}$), wherein x corresponds to the threshold percentage defining the probability of hypoglycemia, wherein the algorithm accounts for past uncertainty regarding at least one of a calibration routine of the user, a day of use for the sensor, and a sensor lot via the database;
   calculating a standard correction insulin dose ($I_g$) utilizing an insulin sensitivity factor (IS) of a user and the pre-set target glucose level;
   calculating a hypoglycemia-averse correction insulin dose ($I_{hypo(x)\%}$) using the insulin sensitivity factor of the user and the calculated level on the cumulative frequency distribution;
   comparing the standard correction insulin dose with the hypoglycemia-averse correction insulin dose; and
   selecting the minimum of the correction insulin doses; and
   adjusting the standard correction insulin bolus administered to the user for the corresponding meal via the selected insulin dose to reduce hypoglycemia risk of the user after consuming the corresponding meal.

3. The method of claim 2 further comprising defining the ($g_{x\%}$) as ($g_{50\%}$) and performing the following calculation:

$$g_{5\%} = g - 1.6449 \cdot \sigma_g.$$

4. The method of claim 2 further comprising setting the ($g_t$) as shown below:

$$g_t = 110 \frac{mg}{dl}.$$

5. The method of claim 2 further comprising setting a hypoglycemia threshold as shown below, $$T_{hypo} = 70 \frac{mg}{dl}$$

and subtracting the ($T_{hypo}$) from the ($g_{x\%}$) in the calculation of the ($I_{hypo(x)\%}$).

6. The method of claim 2 further comprising calculating the standard correction insulin dose by:

$$I_g = \frac{(g - g_t)}{IS}.$$

7. The method of claim 2 further comprising defining the ($g_{x\%}$) as ($g_{50\%}$), designating the ($I_{hypo(x)\%}$) as ($I_{hypo5\%}$) and calculating the hypoglycemia-averse correction insulin dose by:

$$I_{hypo5\%} = \frac{g_{5\%} - T_{hypo}}{IS}.$$

8. The method of claim 2 further comprising removing the standard correction insulin bolus administered to the user for the corresponding meal when the selected insulin dose is negative.

9. The method of claim 2 further comprising providing a carbohydrate suggestion when the selected insulin dose is negative.

10. The method of claim 2 further comprising setting the ($g_x\%$) as at least one of ($g_{10\%}$), ($g_{15\%}$) and ($g_{20\%}$).

11. A bolus calculator to adjust a standard correction insulin bolus administered to a user to reduce hypoglycemia risk after consuming a corresponding meal via an account for continuous glucose monitoring noise of a sensor imbedded in the user, the bolus calculator comprising:
   a processor that when activated is configured to:
      couple the bolus calculator to a database;
      receive a glucose measurement (g) from the sensor embedded in the user;
      execute an algorithm defining a pre-set target glucose level ($g_t$), a threshold percentage defining a probability of hypoglycemia ($P_{hypo}$), and a standard deviation ($\sigma_g$) defining an uncertainty of the glucose measurement (g) from the sensor of the user;

calculate a level ($g_{x\%}$), wherein x corresponds to the threshold percentage defining the probability of hypoglycemia, via use of the glucose measurement, the standard deviation, and a parameter on a normal cumulative distribution, wherein the algorithm accounts for past uncertainty regarding at least one of a calibration routine of the user, a day of use for the sensor, and a sensor lot via the database;

calculate a standard correction insulin dose ($I_g$) utilizing an insulin sensitivity factor (IS) of a user and the pre-set target glucose level;

calculate a hypoglycemia-averse correction insulin dose ($I_{hypo(x)\%}$) using the insulin sensitivity factor of the user and the calculated level on the cumulative frequency distribution;

compare the standard correction insulin dose with the hypoglycemia-averse correction insulin dose;

select the minimum of the correction insulin doses; and adjust the standard correction insulin bolus administered to the user for the corresponding meal via the selected insulin dose to reduce hypoglycemia risk of the user after consuming the corresponding meal.

12. The bolus calculator of claim 11 wherein the algorithm is configured to define the ($g_{x\%}$) as ($g_{50\%}$) and perform the calculation below:

$$g_{5\%} = g - 1.6449 \cdot \sigma_g.$$

13. The bolus calculator of claim 11 wherein the algorithm is configured to set the ($g_t$) as shown below:

$$g_t = 110 \frac{mg}{dl}.$$

14. The bolus calculator of claim 11 wherein the algorithm is configured to set a hypoglycemia threshold as shown below, $$T_{hypo} = 70 \frac{mg}{dl}$$

and subtracting the ($T_{hypo}$) from the ($g_{x\%}$) in the calculation of the ($I_{hypo(x)\%}$).

15. The bolus calculator of claim 11 wherein the algorithm is configured to calculate the standard correction insulin dose by:

$$I_g = \frac{(g - g_t)}{IS}.$$

16. The bolus calculator of claim 11 wherein the algorithm is configured to define the ($g_{x\%}$) as ($g_{5\%}$), designate the $I_{hypo(x)\%}$ as $I_{hypo5\%}$, and calculate the hypoglycemia-averse correction insulin dose by:

$$I_{hypo5\%} = \frac{g_{5\%} - T_{hypo}}{IS}.$$

17. The bolus calculator of claim 11 wherein the algorithm is configured to remove a corresponding meal bolus when the selected insulin dose is negative.

18. The bolus calculator of claim 11 wherein the algorithm is configured to provide a carbohydrate suggestion when the selected insulin dose is negative.

19. The bolus calculator of claim 11, wherein the algorithm is configured to set the level ($g_{x\%}$) as at least one of ($g_{10\%}$), ($g_{15\%}$) and ($g_{20\%}$).

20. The method of claim 2, wherein the processor automatically selects the threshold percentage.

21. The method of claim 2, wherein the standard correction insulin bolus is administered to the user via an insulin pump or by injection.

22. The method of claim 2, further comprises accounting for active insulin recently injected into the user, via the bolus calculator shifting:

the glucose target ($\hat{g}$) by a glucose equivalent for the active insulin ($g_i$), where $\hat{g}_t = g_t + g_i$;

the hypoglycemia threshold ($T_{hypo}$) by the glucose equivalent for the active insulin ($g_i$), where $\hat{T}_{hypo} = T_{hypo} + g_i$, and wherein the standard correction insulin dose is then calculated by:

$$I_g = \frac{g - \hat{g}_t}{IS}$$

and the hypoglycemia-averse correction insulin dose by:

$$I_{hypox\%} = \frac{g_{x\%} - \hat{T}_{hypo}}{IS}.$$

23. The bolus calculator of claim 19, wherein the processor automatically selects between percentages (x %) to set the level ($g_{x\%}$).

* * * * *